United States Patent
Blondino et al.

(10) Patent No.: US 7,501,113 B2
(45) Date of Patent: *Mar. 10, 2009

(54) AEROSOL FORMULATIONS AND AEROSOL DELIVERY OF BUPRENORPHINE

(75) Inventors: Frank E. Blondino, Richmond, VA (US); Justin Poklis, Chapel Hill, NC (US); Matthew Baker, Richmond, VA (US)

(73) Assignee: Philip Morris USA Inc., Richmond, VA (US)

( * ) Notice: Subject to any disclaimer, the term of this patent is extended or adjusted under 35 U.S.C. 154(b) by 801 days.

This patent is subject to a terminal disclaimer.

(21) Appl. No.: 10/734,150

(22) Filed: Dec. 15, 2003

(65) Prior Publication Data

US 2004/0151670 A1  Aug. 5, 2004

Related U.S. Application Data

(60) Provisional application No. 60/444,622, filed on Feb. 4, 2003.

(51) Int. Cl.
*A61K 9/12* (2006.01)
*A61M 16/00* (2006.01)
*A61M 16/12* (2006.01)

(52) U.S. Cl. .................... 424/45; 514/958; 128/200.14; 128/203.12; 128/203.16

(58) Field of Classification Search ................. 424/45; 514/958; 128/200.14, 203.12, 203.16
See application file for complete search history.

(56) References Cited

U.S. PATENT DOCUMENTS

| | | | |
|---|---|---|---|
| 5,607,691 A | 3/1997 | Hale et al. | |
| 5,637,314 A | 6/1997 | Sharpe et al. | |
| 5,743,251 A | 4/1998 | Howell et al. | |
| 5,837,280 A | 11/1998 | Kenealy et al. | |
| 6,228,864 B1 | 5/2001 | Smith et al. | |
| 6,231,594 B1 | 5/2001 | Dae | |
| 6,234,167 B1 * | 5/2001 | Cox et al. | 128/200.14 |
| 6,312,717 B1 | 11/2001 | Molinoff et al. | |
| 6,383,471 B1 | 5/2002 | Chen et al. | |
| 6,501,052 B2 * | 12/2002 | Cox et al. | 219/486 |
| 6,516,796 B1 * | 2/2003 | Cox et al. | 219/200.23 |
| 6,557,552 B1 * | 5/2003 | Cox et al. | 128/203.27 |
| 6,568,390 B2 * | 5/2003 | Nichols et al. | 128/203.16 |
| 6,682,716 B2 * | 1/2004 | Hodges et al. | 424/45 |
| 6,701,922 B2 * | 3/2004 | Hindle et al. | 128/203.27 |
| 6,737,043 B2 | 5/2004 | Rabinowitz | |
| 6,766,220 B2 * | 7/2004 | McRae et al. | 700/266 |
| 6,799,572 B2 * | 10/2004 | Nichols et al. | 128/203.26 |
| 6,854,461 B2 * | 2/2005 | Nichols et al. | 128/203.16 |
| 6,883,516 B2 * | 4/2005 | Hindle et al. | 128/200.14 |
| 6,923,179 B2 * | 8/2005 | Gupta et al. | 128/203.17 |
| 7,040,314 B2 * | 5/2006 | Nguyen et al. | 128/203.12 |
| 7,077,130 B2 * | 7/2006 | Nichols et al. | 128/203.26 |
| 7,117,867 B2 * | 10/2006 | Cox et al. | 128/200.14 |
| 7,128,067 B2 * | 10/2006 | Byron et al. | 128/200.14 |
| 7,147,170 B2 * | 12/2006 | Nguyen et al. | 239/13 |
| 7,163,014 B2 * | 1/2007 | Nichols et al. | 128/203.26 |
| 7,167,776 B2 * | 1/2007 | Maharajh et al. | 700/266 |
| 7,173,222 B2 * | 2/2007 | Cox et al. | 219/486 |
| 2002/0058009 A1 | 5/2002 | Bartus et al. | |
| 2003/0017116 A1 | 1/2003 | Rabinowitz et al. | |
| 2004/0016427 A1 * | 1/2004 | Byron et al. | 128/200.14 |
| 2004/0079368 A1 * | 4/2004 | Gupta et al. | 128/203.12 |
| 2004/0081624 A1 * | 4/2004 | Nguyen et al. | 424/44 |
| 2004/0129793 A1 * | 7/2004 | Nguyen et al. | 239/13 |
| 2004/0170405 A1 * | 9/2004 | Sherwood et al. | 392/397 |
| 2004/0202617 A1 * | 10/2004 | Rabinowitz et al. | 424/46 |
| 2004/0223917 A1 * | 11/2004 | Hindle et al. | 424/45 |
| 2004/0223918 A1 * | 11/2004 | Pham et al. | 424/45 |
| 2005/0079137 A1 * | 4/2005 | Blondino et al. | 424/45 |
| 2005/0126624 A1 * | 6/2005 | Pellizzari | 136/253 |
| 2005/0133029 A1 * | 6/2005 | Nichols et al. | 128/203.26 |
| 2005/0143866 A1 * | 6/2005 | McRae et al. | 700/299 |
| 2005/0205084 A1 * | 9/2005 | Gupta et al. | 128/200.14 |

FOREIGN PATENT DOCUMENTS

WO   WO00/00215 A1   1/2000

OTHER PUBLICATIONS

Notification of Transmittal of the International Search Report or the Declaration dated Jun. 17, 2004 for PCT/US03/39819.
Written Opinion for PCT/US03/39819 dated Nov. 17, 2004.
International Preliminary Examination Report for PCT/US03/39819 dated Jun. 7, 2005.

* cited by examiner

*Primary Examiner*—Mina Haghighatian
(74) *Attorney, Agent, or Firm*—Buchanan Ingersoll & Rooney PC

(57) ABSTRACT

A liquid aerosol formulation comprising at least one thermally stable active ingredient selected from the group consisting of buspirone, buprenorphine, triazolam, cyclobenzaprine, zolpidem, pharmaceutically acceptable salts and esters thereof and derivatives thereof. The liquid formulation can include an organic solvent such as propylene glycol and one or more optional excipients. The active ingredient can be present in an amount of 0.01 to 5 wt. % and the formulation can be heated to provide a vapor which forms an aerosol having a mass median aerodynamic diameter of less than 3 μm.

11 Claims, 3 Drawing Sheets

US 7,501,113 B2

AEROSOL FORMULATIONS AND AEROSOL DELIVERY OF BUPRENORPHINE

This application claims priority under 35 U.S.C. §119 to U.S. Provisional Application No. 60/444,622 entitled AEROSOL FORMULATIONS AND AEROSOL DELIVERY OF BUSPIRONE, BUPRENORPHINE, TRIAZOLAM, CYCLOBENZAPRINE AND ZOLPIDEM, filed Feb. 4, 2003, the entire content of which is hereby incorporated by reference.

1. FIELD OF THE INVENTION

The invention relates generally to an liquid aerosol formulation. More specifically, the invention relates to a liquid aerosol formulation comprising at least one thermally stable active ingredient selected from the group consisting of buspirone, buprenorphine, triazolam, cyclobenzaprine, zolpidem, pharmaceutically acceptable salts and esters thereof and derivatives thereof. The invention further relates to aerosol generating devices and methods for generating aerosols.

2. BACKGROUND OF THE INVENTION

Aerosols are gaseous suspensions of fine solid or liquid particles. Aerosols are useful in a wide variety of applications. For example, medicated liquids may be administered in aerosol form. Medicated aerosols include materials that are useful in the treatment of respiratory ailments. In such applications, the aerosols may be produced by an aerosol generator and inhaled into a patient's lungs.

Aerosol generators are known that include a heated tube for vaporizing liquid. For example, commonly assigned U.S. Pat. No. 5,743,251, which is incorporated herein by reference in its entirety, discloses an aerosol generator including a tube and a heater operable to heat the tube to a sufficient temperature to volatilize liquid in the tube. It is disclosed that the volatilized material expands out of an end of the tube and admixes with ambient air, thereby forming an aerosol.

Other aerosol generators including a heated tube for vaporizing liquids to produce an aerosol are described in commonly-assigned U.S. Pat. No. 6,234,167, U.S. patent application Ser. No. 09/956,966 filed Sep. 21, 2001 and Ser. No. 10/003,437 filed Dec. 6, 2001 and U.S. Provisional Application No. 60/408,894, filed Sep. 6, 2002, each being incorporated herein by reference in its entirety.

3. SUMMARY OF THE INVENTION

One embodiment of the invention provides a liquid aerosol formulation comprising at least one thermally stable active ingredient selected from the group consisting of buspirone, buprenorphine, triazolam, cyclobenzaprine, zolpidem, pharmaceutically acceptable salts and esters thereof and derivatives thereof. The formulation may contain any desired amount of the active ingredient. In a preferred embodiment, the formulation may contain 0.01 to 5% by weight of the thermally stable active ingredient.

The liquid aerosol formulation may further comprise an organic solvent. The organic solvent may be, but is not limited to a short chain ($C_1$-$C_6$) alcohol. The short chain ($C_1$-$C_6$) alcohol may be, but is not limited to, glycerin, ethylene glycol, diethylene glycol, propylene glycol, n-propyl alcohol, isopropyl alcohol, butanol, ethanol, sorbitol, dipropylene glycol, tripropylene glycol, and hexylene glycol. Preferably, the organic solvent is propylene glycol or dipropylene glycol.

The liquid aerosol formulation may further comprise at least one pharmaceutically acceptable excipient. The excipient may be, but is not limited to, antioxidants, stabilizing agents, flavoring agents, solubilizers, cosolvents, preservatives and combinations thereof. Preferably, the cosolvent is ethanol, water, glycerol and/or diethyl ether. Preferably, the solubilizer is ethanol, isopropanol, butanol, benzyl alcohol, ethylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives, and/or mixtures thereof.

In a preferred embodiment, the thermally stable active ingredient comprises buspirone and the organic solvent is propylene glycol.

In a preferred embodiment, the thermally stable active ingredient comprises buprenorphine and the organic solvent is propylene glycol.

In a preferred embodiment, the thermally stable active ingredient comprises triazolam and the organic solvent is propylene glycol.

In a preferred embodiment, the thermally stable active ingredient comprises cyclobenzaprine and the organic solvent is propylene glycol.

In a preferred embodiment, the thermally stable active ingredient comprises zolpidem and the organic solvent is propylene glycol.

According to one embodiment, the invention provides a method of generating an aerosol comprising supplying a liquid aerosol formulation to a flow passage, heating the liquid aerosol formulation in the flow passage so as to volatilize a liquid component thereof and form a vapor which exits from an outlet of the flow passage, and contacting the vapor with a gaseous medium so as to form an aerosol, wherein the liquid aerosol formulation includes at least one thermally stable active ingredient selected from the group consisting of buspirone, buprenorphine, triazolam, cyclobenzaprine, zolpidem, pharmaceutically acceptable salts and esters thereof. For drug delivery, the liquid aerosol formulation preferably comprises particles of propylene glycol having a mass median aerodynamic diameter (MMAD) of less than 3 µm. The liquid aerosol formulation may further include at least one thermally stable active ingredient and the aerosol comprises particles of the thermally stable active ingredient having an MMAD of less than 3 µm.

In a preferred embodiment, the thermally stable active ingredient comprises buspirone and the aerosol comprises buspirone particles having an MMAD of less than 3 µm.

In a preferred embodiment, the thermally stable active ingredient comprises buprenorphine and the aerosol comprises buprenorphine particles having an MMAD of less than 3 µm.

In a preferred embodiment, the thermally stable active ingredient comprises triazolam and the aerosol comprises triazolam particles having an MMAD of less than 3 µm.

In a preferred embodiment, the thermally stable active ingredient comprises cyclobenzaprine and the aerosol comprises cyclobenzaprine particles having an MMAD of less than 3 µm.

In a preferred embodiment, the thermally stable active ingredient comprises zolpidem and the aerosol comprises zolpidem particles having an MMAD of less than 3 µm.

In a preferred embodiment, the flow passage is a capillary sized flow passage and the aerosol is formed in a mouthpiece of a handheld inhaler. The aerosol may include particles of the thermally stable active ingredient having an MMAD of 0.1 to 2.5 μm and the aerosol preferably has a recovery rate of at least 90% during generation of the aerosol. Preferably, the flow passage is heated by a resistance heater located in a handheld inhaler, the inhaler including a power supply and control electronics which controls supply of electrical power to the heater as a function of a resistance target in a range of 0.5 to 1 ohm.

According to one embodiment, the invention provides an aerosol generator, comprising a flow passage adapted to receive a liquid aerosol formulation from a liquid supply, the liquid aerosol formulation comprising at least one thermally stable active ingredient selected from the group consisting of buspirone, buprenorphine, triazolam, cyclobenzaprine, zolpidem, pharmaceutically acceptable salts and esters thereof and derivatives thereof, and a heater operable to heat the liquid formulation in at least a portion of the flow passage sufficiently to vaporize the liquid formulation and generate an aerosol containing the active ingredient. The aerosol generator may comprise a hand-held inhaler having a mouthpiece, the flow passage comprising a capillary sized flow passage having an outlet in fluid communication with an interior of the mouthpiece. In a preferred embodiment, the heater is a resistance heater comprising a section of a metal capillary tube and the flow passage comprises the interior of the metal capillary tube. The aerosol generator may comprise a hand-held inhaler having a power supply and control electronics which controls supply of electrical power to the heater as a function of a control parameter selected to achieve boiling of the liquid formulation in the flow passage. The liquid supply may comprise a reservoir containing the liquid formulation under a pressure of no greater than about atmospheric pressure.

4. BRIEF DESCRIPTION OF THE DRAWINGS

Various preferred embodiments of the invention will be readily understood by reference to the following detailed description and the accompanying drawings, in which.

5. DETAILED DESCRIPTION OF THE PREFERRED EMBODIMENTS OF THE INVENTION

Figure 1:
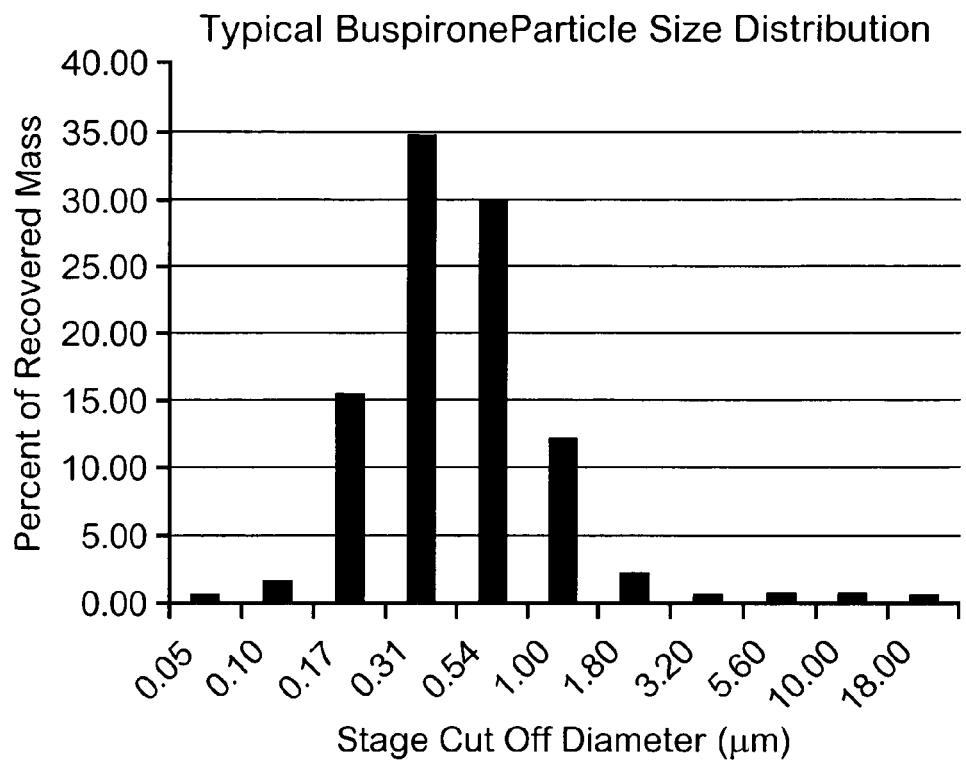
FIG. 1 shows a bar graph illustrating the typical buspirone particle size distribution.

Liquid aerosol formulations, aerosol generating devices and methods for generating aerosols are provided.

The liquid aerosol formulations can provide aerosols having selected compositions and controlled particle sizes. The liquid aerosol formulations are suitable for different applications including systemic delivery of medicaments. For example, for drug delivery applications via inhalation, the formulations comprise aerosols having a desirable mass median aerodynamic diameter (MMAD) for targeted delivery. For pulmonary delivery, particles of smaller size are desired than for tracheobronchial delivery or delivery to the oropharynx or mouth. In preferred embodiments, the aerosols have a controlled particle size that is effective to achieve pulmonary delivery of drug formulations.

The liquid aerosol formulation preferably includes an organic solvent and at least one thermally stable active ingredient. The thermally stable active ingredients may be selected from the group consisting of buspirone, buprenorphine, triazolam, cyclobenzaprine, zolpidem, pharmaceutically acceptable salts and esters thereof and derivatives thereof. The thermally stable active ingredients can be somewhat or completely soluble in the liquid aerosol formulation. In addition, the liquid aerosol formulation is preferably propellant free.

Buspirone, buprenorphine, triazolam, cyclobenzaprine, zolpidem, pharmaceutically acceptable salts and esters thereof and derivatives thereof are sufficiently soluble in an organic solvent to form solutions at ambient conditions. The concentration of buspirone, buprenorphine, triazolam, cyclobenzaprine, zolpidem, pharmaceutically acceptable salts and esters in the solution can be varied to control the amount of the active ingredient in such aerosols.

The liquid aerosol formulation may further comprise additional active ingredients, in combination with buspirone, buprenorphine, triazolam, cyclobenzaprine, zolpidem, pharmaceutically acceptable salts and esters thereof and/or derivatives thereof.

The liquid aerosol formulation may further comprise an organic solvent. Examples of organic solvents include, but are not limited to, short chain ($C_1$-$C_6$) alcohols, such as n-propyl alcohol, isopropyl alcohol, butanol, ethanol, glycerin, ethylene glycol, diethylene glycol, propylene glycol, sorbitol, dipropylene glycol, tripropylene glycol, and hexylene glycol. Preferred short chain alcohols are propylene glycol and dipropylene glycol. Propylene glycol (PG) is especially preferred.

The liquid aerosol formulation may also include any pharmaceutically acceptable excipient. Such excipients may include, but are not limited to, antioxidants, stabilizing agents, flavoring agents, solubilizers, cosolvents, preservatives and combinations thereof.

Preferably, the cosolvent is ethanol, water, glycerol and diethyl ether. Preferably, the solubilizer is ethanol, isopropanol, butanol, benzyl alcohol, ethylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives or mixtures thereof.

In a preferred embodiment, the liquid aerosol formulation is flowed through a capillary sized flow passage in which the liquid is heated to a sufficiently high temperature to vaporize the liquid. The vapor exits the flow passage and admixes with gas, preferably ambient air, to produce an aerosol which is inhaled by a user. The size of the aerosol particles thus produced can be controlled for delivery to the lung.

The capillary passage can have different transverse cross-sectional shapes, such as round, oval, triangular, square, rectangular, other polygonal shapes, or the like, as well as other non-geometric shapes. Different portions of the capillary passage can have different cross-sectional shapes. As described below, the size of the capillary passage can be defined by its transverse cross-sectional area. For a capillary passage having a round cross-section, the size of the flow passage may be defined by its diameter. Alternatively, the capillary passage may be non-circular in cross section and the size of the capillary passage may be defined by its width. For example, the capillary passage can have a maximum width of 0.01 to 10 mm, preferably 0.05 to 1 mm, and more preferably 0.1 to 0.5 mm. Alternatively, the capillary passage can be defined by its transverse cross sectional area, which can be $8 \times 10^{-5}$ to 80 $mm^2$, preferably $2 \times 10^{-3}$ to $8 \times 10^{-1}$ $mm^2$, and more preferably $8 \times 10^{-3}$ to $2 \times 10^{-1}$ $mm^2$.

Details of an aerosol generator which can be used to aerosolize the liquid formulation are described in commonly assigned U.S. Pat. Nos. 5,743,251; 6,234,167 and 6,516,796, the entire disclosures of which are hereby incorporated by reference. Other suitable aerosol generators are described in commonly assigned U.S. patent application Ser. No. 10/341,521 filed Jan. 14, 2003, the entire disclosure of which is hereby incorporated by reference. Control schemes for heating the flow passage are describe din commonly assigned U.S. Pat. No. 6,501,052, the entire disclosure of which is hereby incorporated by reference, and in commonly assigned U.S. patent application Ser. No. 10/206,320 filed Jul. 29, 2002, the entire disclosure of which is hereby incorporated by reference.

As described in commonly-assigned U.S. Provisional Patent Application No. 60/408,295, filed Sep. 6, 2002, which is incorporated herein by reference in its entirety, embodiments of the capillary passage can comprise an outlet section, which controls the velocity of vapor exiting the outlet end of the capillary passage, i.e, the exit velocity of the vapor, so as to control the particle size of aerosol generated by the aerosol generating device.

The material forming the capillary passage can be any suitable material, including metals, plastics, polymers, ceramics, glasses, or combinations of these materials. Preferably, the material is a heat-resistant material capable of withstanding the temperatures and pressures generated in the capillary passage, and also resisting the repeated heating cycles utilized to generate multiple doses of aerosols. In addition, the material forming the capillary passage preferably is non-reactive with the liquid that is aerosolized.

In another alternative embodiment, the capillary passage can be formed in a polymer, glass, metal and/or ceramic monolithic or multilayer (laminated) structure (not shown). Suitable ceramic materials for forming the capillary passage include, but are not limited to, alumina, zirconia, silica, aluminum silicate, titania, yttria-stabilized zirconia, or mixtures thereof. A capillary passage can be formed in the monolithic or multilayer body by any suitable technique, including, for example, machining, molding, extrusion, or the like.

In embodiments, the capillary passage can have a length from 0.5 to 10 cm, and preferably from 1 to 4 cm.

The liquid aerosol formulation supplied from a liquid source is heated in the capillary passage to form a vapor during operation of the aerosol generating device. In a preferred embodiment, the capillary comprises metal tubing heated by passing an electrical current along a length of the capillary tubing via a first electrode and a second electrode. However, as described above, the capillary passage can have other alternative constructions, such as a monolithic or multilayer construction, which include a heater such as a resistance heating material positioned to heat the fluid in the capillary passage. For example, the resistance heating material can be disposed inside of, or exterior to, the capillary passage.

The capillary passage may comprise an electrically conductive tube provided with a downstream electrode and an upstream electrode. In this embodiment, the capillary is a controlled temperature profile (CTP) construction, such as disclosed in copending and commonly assigned U.S. application Ser. No. 09/957,026, filed Sep. 21, 2001, which is incorporated herein by reference in its entirety. In the controlled temperature profile capillary, the downstream electrode has an electrical resistance sufficient to cause it to be heated during operation of the aerosol generating device, thereby minimizing heat loss at the outlet end of the capillary tube.

The tube forming the capillary passage can be made entirely of stainless steel or any other suitable electrically conductive materials. Alternatively, the tube can be made of a non-conductive or semi-conductive material incorporating a heater made from an electrically conductive material, such as platinum. Electrodes connected at spaced positions along the length of the tube or heater define a heated region between the electrodes. A voltage applied between the two electrodes generates heat in the heated region of the capillary passage based on the resistivity of the material(s) making up the tube or heater, and other parameters such as the cross-sectional area and length of the heated region section. As the fluid flows through the capillary passage into the heated region between the first and second electrodes, the fluid is heated and converted to a vapor. The vapor passes from the heated region of the capillary passage and exits from the outlet end. In some preferred embodiments, the volatilized fluid is entrained in ambient air as the volatilized fluid exits from the outlet, causing the volatilized fluid to condense into small droplets and form a condensation aerosol. In a preferred embodiment, the MMAD of the droplet size is 0.1 to 2.5 µm.

The temperature of the liquid in the capillary passage can be calculated based on the measured or calculated resistance of the heating element. For example, the heating element can be a portion of a metal tube, or alternatively a strip or coil of resistance heating material. Control electronics can be used to regulate the temperature of the capillary passage by monitoring the resistance of the heater. For example, the control electronics can control the temperature profile of the capillary passage during operation of the aerosol generating device. The control electronics can also control the output of the display. The display is preferably a liquid crystal display (LCD). The display can depict selected information pertaining to the condition or operation of the aerosol generating device. The control electronics can also control the operation of one or more valves during operation of the aerosol generating device; monitor the initial pressure drop caused by inhalation and sensed by the pressure sensor; and monitor the condition of the battery unit that provides electrical power to components of the aerosol generating device.

Preferably, the aerosol particles have a MMAD between about 0.1 µm and about 2.5 µm. As described above, the aerosol generating device can provide aerosols having a controlled particle size, including aerosols sized for the targeted delivery of drugs to the lung. These aerosols offer a number of advantages for delivering drugs to the deep lung. For example, mouth and throat deposition are minimized, while deposition in the deep lung is maximized, especially when combined with a breath hold. Moreover, when using a suitable hydrophilic carrier, deposition may be further enhanced by hygroscopic growth.

The aerosol generating device preferably generates aerosols in which 95% of the aerosol particles (aerosol droplets) have a size in the range between about 0.1 µm to about 2.5 µm. The aerosol generating device preferably incorporates a processor chip for controlling the generation process. The processor, with suitable sensors, also triggers the aerosol generation at any desired time during an inhalation. The drug to be aerosolized is provided with a carrier. By the choice of suitable hydrophilic carriers, the aerosol generating device can take advantage of hygroscopic growth in the respiratory system.

Operation of the preferred aerosol generating device for delivering aerosolized thermally stable active ingredients is as follows. First, a liquid aerosol formulation including at least one thermally stable active ingredient is delivered to the heated capillary passage. The liquid vaporizes in the capillary passage and exits as a vapor jet from the open end of the capillary passage. The vapor jet entrains and mixes with ambient air, and forms a highly concentrated, fine aerosol. As described above, application of heat to vaporize the liquid is typically achieved by resistive heating from passing an electric current through the heater. The applied power is adjusted to maximize the conversion of the fluid into a vapor.

As will be appreciated, the aerosol generating device is capable of controlled vaporization and aerosol formation of drug formulations. The aerosol generating device can provide immediate delivery of aerosol to a patient, thereby not wasting lung capacity, which may be limited due to the health of the patient. Also, the aerosol generating device can provide consistent delivery of controlled amounts of drug formulation to a patient. In addition, in preferred embodiments, the aerosol generated by the aerosol generating device including a capillary passage is only slightly affected by relative humidity and temperature.

EXAMPLES

Examples were conducted to demonstrate features of the invention. The examples are not intended to and should not be interpreted as limiting the invention.

Example 1

Buspirone Aerosol

A suitable aerosol was generated using buspirone (8-[4-[4-(2-pyrimidinyl)-1-piperazinyl]butyl]-8-azaspiro[4,5]decane-7,9-dione monohydrochloride) dissolved in propylene glycol (PG).

Experiments were performed to determine if a chemically stable 0.5 μm busprione (BUS) aerosol could be generated using a 28 gauge, 44 mm long steel capillary using a flow rate of 5 mg/sec. The aerosol particle size was determined and chemical stability of buspirone in the generated aerosol was evaluated. Buspirone was purchased from Sigma Aldrich Chemical Co. Propylene glycol was purchased from Dow Chemical Co.

Forced Degradation Studies

Buspirone was dissolved in acidic and basic solutions and heated to 50 degrees Celsius for 1 hour to promote acid and base catalyzed hydrolysis. Buspirone was also subjected to peroxide with heating to 50 degrees Celsius for 1 hour to promote oxidation. As a final stability check, solid buspirone was subjected to heating with a differential scanning calorimeter. Conditions were optimized to produce thermal degradation products by heating to 350 degrees Celsius.

Sham Determinations

Sham determinations were performed for each set of experiments to determine an "expected" amount of active per capillary aerosol generator (CAG) activation. This was performed by running the equipment at a target resistance of 0.2 ohms, which pumped out the solution of buspirone in PG as a liquid instead of an aerosol. The result was collected on a Kimwipe which was placed into sample solvent and sonicated. This process was performed in triplicate. Two solution concentrations of about 0.5% and about 2% of buspirone in PG were prepared.

Dose Capture and Degradation Determinations

Dose capture determinations were conducted (Table 1). For dose capture runs 1-6, the device was actuated once, the aerosol collected in acidified water, diluted to 40 mL. Runs 7-12 were performed as above, except distilled de-ionized water was used instead of acidified water. For runs 13-33, the device was actuated 4 times, the aerosol was collected in 8 mL of sample solvent, and analyzed for buspirone and degradation products using the "stability indicating" assay. Intact buspirone was calculated. The extent of degradation was evaluated by assuming that the degradation products had similar extinction coefficients as the parent at the wavelength of interest.

The initial dose capture experiments (runs 1-6) performed at a buspirone concentration of 0.5% in PG indicated that buspirone was stable during the aerosolization process. A 2% solution of buspirone in PG was prepared and aerosolized. Initial investigations (runs 7-15) indicated that an energy of greater than about 80 J was required to aerosolize buspirone. Greater energy was required to minimize throat deposition. This was further refined to a target resistance of 0.605 ohms to provide an energy input of about 90 J. Using these parameters, 104% of the buspirone expected was aerosolized and collected.

After evaluation of the data, it was determined that buspirone should be thermally stressed with a DSC to produce a degradation profile thought to be more representative of buspirone degradation after aerosolization via the CAG. In doing so, thermal degradation products were produced under the conditions stated above. This provided an indication of retention times for potential degradation products of buspirone after aerosolization using the CAG. The samples collected at a target resistance of 0.605 ohms were evaluated for degradation. As can be seen in Table 2, degradation was minimal with an average degradation of 0.25% of the active, while active recovery was 104%. During the analysis, 9 potential degradation products were produced which matched the retention times of products observed after subjected to heating. The major degradation peak was hypothesized to contain multiple analytes and accounted for approximately 0.09% of the degradation observed. The other 8 peaks accounted for approximately 0.02% each. Of the nine peaks observed in the collected samples after aerosol generation, three were found in the standard at levels of approximately 0.01%. In addition, more degradation products were formed after heating compared to the sample collected using the dose capture apparatus after aerosolization.

Particle Size Determinations

Aerosol particle size was determined using the 10-stage MOUDI operated at 30 L/min. The sample foils were placed in beakers, 10 mL of sample solvent was added, and the beakers swirled thoroughly. For the USP throat, 10 mL of sample solvent was added and shaken thoroughly. Wall losses were assessed by washing the MOUDI walls with a Kimwipe dipped in sample solvent. The same 10 mL of mobile phase was used to wash the walls of all the stages. The collected samples were analyzed.

Early dose capture experiments indicated that buspirone could be aerosolized and captured. Due to the high recovery, it was suspected that buspirone was relatively stable upon heating and during aerosolization with the CAG. After determining energy requirements for aerosolizing buspirone, particle size determinations were performed (Table 3). At energies of approximately 77 J (runs 8 and 10), a large percentage, greater than 40%, of the recovered buspirone was found on the throat. At the refined target resistance of 0.605 ohms (runs 11-15), the energies were approximately 87 J. This produced monomodal aerosols (FIG. 1) having mass median aerodynamic diameters (MMAD) of approximately 0.30 microns. Recoveries for these experiments exceeded 100% and had throat depositions of less than 5%.

Based upon the reproducible effective aerosolization, suitable particle size, acceptable recoveries, and the ability to deliver high concentrations of buspirone, it was concluded that buspirone was a compound suitable for aerosolization.

TABLE 1

Dose capture determinations

| Run Number | Formulation Buspirone % | Formulation Flow Rate (mg/sec) | Target Resistance (ohms) | Energy (J) | Air Flow Rate (L/min) | Dose Capture (%) |
|---|---|---|---|---|---|---|
| 1 | 0.5 | 5 | 0.610 | 88.64 | 0.5 | 145 |
| 2 | 0.5 | 5 | 0.610 | 89.82 | 0.5 | 101 |
| 3 | 0.5 | 5 | 0.610 | 90.90 | 0.5 | 102 |
| 4 | 0.5 | 5 | 0.610 | 90.94 | 0.5 | 94 |
| 5 | 0.5 | 5 | 0.610 | 91.65 | 0.5 | 94 |
| 6 | 0.5 | 5 | 0.610 | 91.70 | 0.5 | 98 |
| 7-9 | 2.0 | 5 | 5.90 | 70.79[1] | 0.5[1] | 9[1] |
| 10-12 | 2.0 | 5 | 0.610 | 87.92[1] | 0.5[1] | 102[1] |
| 13-15 | 2.0 | 5 | 0.595 | 80.36[2] | 0.5[2] | 102[1] |
| 16-18 | 2.0 | 5 | 0.610 | 98.99[2] | 0.5[2] | 103[1] |
| 19-23 | 2.0 | 5 | 0.610 | 98.71[3] | 0.5[3] | 95[3] |
| 24-28 | 2.0 | 5 | 0.600 | 80.84[3] | 0.5[3] | 105[3] |
| 29-33 | 2.0 | 5 | 0.605 | 88.86[3] | 0.5[3] | 104[3] |

[1]Mean of 3 determinations
[2]Mean of 12 determinations (3 dose captures of 4 actuations)
[3]Mean of 20 determinations (5 dose captures of 4 actuations)

TABLE 2

Percent degradation determination

| Run Number | Formulation Buspirone % | Target Resistance (ohms) | Energy (J) | Dose Capture (%) | Percent Degradation |
|---|---|---|---|---|---|
| 29 | 2.0 | 0.605 | 88.64 | 105 | 0.10 |
| 30 | 2.0 | 0.605 | 89.82 | 108 | 0.22 |
| 31 | 2.0 | 0.605 | 90.90 | 95 | 0.29 |
| 32 | 2.0 | 0.605 | 90.94 | 107 | 0.30 |
| 33 | 2.0 | 0.605 | 91.65 | 105 | 0.32 |

TABLE 3

Particle size determination

| Run Number | Formulation Buspirone % | Flow Rate (mg/sec) | Target Resistance (ohms) | Energy (J) | MOUDI Number | MMAD (microns) | Material Balance (%) | Throat Deposition (%) | Wall Losses (%) |
|---|---|---|---|---|---|---|---|---|---|
| 1 | 0.5 | 5 | 0.610 | 88.46 | 311 | 0.47 | 39 | 3 | ND |
| 2 | 0.5 | 5 | 0.610 | 88.71 | 312 | 0.32 | 84 | 6 | ND |
| 3 | 0.5 | 5 | 0.610 | 88.61 | 313 | 0.29 | 85 | 4 | ND |
| 4 | 0.5 | 5 | 0.600 | 79.79 | 314 | 0.31 | 100 | 7 | 2 |
| 5 | 0.5 | 5 | 0.610 | 90.74 | 315 | 0.30 | 100 | 10 | 4 |
| 6 | 2.0 | 5 | 0.590 | 68.02 | 316 | 0.54 | 11 | 44 | 6 |
| 7 | 2.0 | 5 | 0.610 | 88.12 | 317 | 0.30 | 98 | 14 | 1 |
| 8 | 2.0 | 5 | 0.595 | 77.14 | 325 | 0.46 | 91 | 44 | 1 |
| 9 | 2.0 | 5 | 0.600 | 83.56 | 326 | 0.30 | 100 | 7 | 2 |
| 10 | 2.0 | 5 | 0.600 | 77.35 | 327 | 0.48 | 98 | 48 | 4 |
| 11 | 2.0 | 5 | 0.605 | 97.09 | 330 | 0.31 | 105 | 4 | 4 |
| 12 | 2.0 | 5 | 0.605 | 87.64 | 331 | 0.30 | 108 | 1 | 3 |
| 13 | 2.0 | 5 | 0.605 | 86.85 | 332 | 0.31 | 102 | 3 | 3 |
| 14 | 2.0 | 5 | 0.605 | 97.44 | 333 | 0.29 | 107 | 2 | 9 |
| 15 | 2.0 | 5 | 0.605 | 97.19 | 334 | 0.32 | 111 | 2 | 3 |

ND—not determined

Example 2

Buprenorphine Aerosol

Experiments were performed to determine if a chemically stable 0.5 μm buprenorphine aerosol could be generated using a 28 gauge, 44 mm long steel capillary using a flow rate of 5 mg/sec. The aerosol particle size was determined and chemical stability of buprenorphine in the generated aerosol was evaluated. Buprenorphine hydrochloride was purchased from Sigma Aldrich Chemical Co. Propylene glycol was purchased from Dow Chemical Co.

Forced Degradation Studies

Buprenorphine was subjected to heating with a differential scanning calorimeter. Conditions were optimized to produce thermal degradation products by heating to 325 degrees Celsius.

Sham Determinations

Sham determinations were performed by running the equipment at a target resistance of 0.2 ohms, which pumped out the solution of buprenorphine in PG as a liquid instead of an aerosol. The result was collected on a Kimwipe, placed into sample solvent and sonicated. This process was performed in triplicate and was analyzed with other analytical samples. Buprenorphine was dissolved in PG at a concentration of approximately 0.2%.

Dose Capture and Degradation Determinations

Dose capture determinations were conducted. See Table 4, which lists each experiment, the number of actuations, the solvent and volume used, and the results. The extent of degradation of buprenorphine was evaluated by assuming that the degradation products had similar extinction coefficients as the parent at the wavelength of interest.

The investigations indicated that an energy of greater than about 70 J was required to aerosolize buprenorphine and minimize throat deposition. This was further refined to a target resistance of 0.595 ohms to provide an energy input of about 70 J. Using these parameters, >95% of the buprenorphine (Table 4 runs 8-12) was aerosolized and collected. Analysis of the samples from runs 8-12 indicated an average degradation of 2%. This was in the form of two proposed degradation products.

Particle Size Determinations

Aerosol particle size was determined using the 10-stage MOUDI operated at 30 L/min. See Table 5, which lists each experiment, the number of actuations, the solvent and volume used, and the results. For the USP throat, 5 mL of sample solvent was added and shaken thoroughly. Wall losses were assessed by washing the MOUDI walls with a Kimwipe dipped in sample solvent. The same sample solvent was used to wash the walls of all the stages. The collected samples were analyzed using the assay method.

Figure 2:
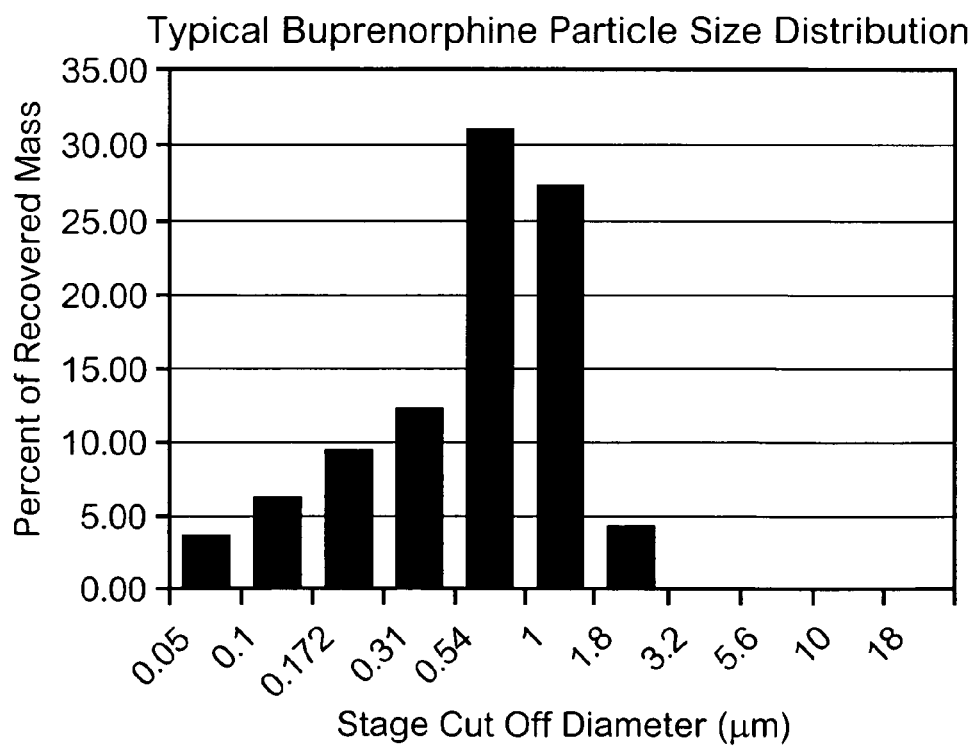
FIG. 2 shows a bar graph illustrating the typical buprenorphine particle size distribution.

Early dose capture experiments indicated that buprenorphine could be aerosolized and captured. After determining energy requirements for aerosolizing buprenorphine, particle size determinations were performed (Table 5). At energies of approximately 70 J (runs 8 through 20), a small percentage, less than about 15%, of the recovered buprenorphine was found on the throat. Runs 8-11 were performed to evaluate throat deposition using a shortened MOUDI consisting of only a couple of stages. Therefore, the MMAD was not determined. At the refined target resistance of 0.595 ohms (runs 18-20), the energies were approximately 71 J. This produced aerosols (FIG. 2) having an average MMAD of approximately 0.44 microns. The average recovery for these experiments exceeded 88% and had throat depositions of less than 3%.

Based upon the reproducible effective aerosolization, suitable particle size, and the ability to deliver adequate quantities of buprenorphine, it was concluded that buprenorphine was a compound suitable for aerosolization.

TABLE 4

Dose capture and degradation determinations

| Run Number | Formulation Busprenorphine % | Formulation Flow Rate (mg/sec) | Target Resistance (ohms) | Energy (J) | Air Flow Rate (L/min) | Number of Actuations | Solvent and Volume | Dose Capture (%) | Percent Degradation |
|---|---|---|---|---|---|---|---|---|---|
| 1 | 0.2 | 5 | 0.600 | 84.93 | 0.5 | 1 | 10 mL DDI | 93 | ND |
| 2 | 0.2 | 5 | 0.610 | 94.95 | 0.5 | 1 | 10 mL DDI | 99 | ND |
| 3 | 0.2 | 5 | 0.620 | 105.83 | 0.5 | 1 | 10 mL DDI | 96 | ND |
| 4 | 0.2 | 5 | 0.610 | 93.11[1] | 0.5 | 2 | 5 mL MP | 82[1] | ND |
| 5 | 0.2 | 5 | 0.610 | 83.95[2] | 0.6[2] | 4 | 10 mL MP | ND | ND |
| 6 | 0.2 | 5 | 0.605 | 84.15[2] | 0.5[2] | 4 | 10 mL MP | ND | ND |
| 7 | 0.2 | 5 | 0.600 | 78.74[2] | 0.6[2] | 4 | 10 mL MP | ND | ND |
| 8 | 0.2 | 5 | 0.595 | 74.91[2] | 0.5[2] | 4 | 10 mL DDI | 96[2] | 2.16[2] |
| 9 | 0.2 | 5 | 0.595 | 74.58[2] | 0.5[2] | 4 | 10 mL DDI | 95[2] | 1.74[2] |
| 10 | 0.2 | 5 | 0.595 | 74.62[2] | 0.5[2] | 4 | 10 mL DDI | 97[2] | 2.27[2] |
| 11 | 0.2 | 5 | 0.595 | 74.82[2] | 0.5[2] | 4 | 10 mL DDI | 103[2] | 1.81[2] |
| 12 | 0.2 | 5 | 0.595 | 74.64[3] | 0.5[3] | 5 | 10 mL DDI | 96[3] | 1.96[3] |

[1]Mean of 2 actuations
[2]Mean of 4 actuations
[3]Mean of 5 actuations
DDI—distilled deionized water
MP—mobile phase
ND—not determined

TABLE 5

Particle size determinations

| Run Number | Formulation (BUP) % | Flow Rate (mg/sec) | Target Resistance (ohms) | Energy (J) | MOUDI Number | Number of Actuations | Solvent and Volume | MMAD (microns) | Material Balance (%) | Throat Deposition (%) | Wall Losses (%) |
|---|---|---|---|---|---|---|---|---|---|---|---|
| 1 | 0.2 | 5 | 0.610 | 94.33 | 340 | 1 | 5 mL DDI | 0.489 | 120.74 | 2.25 | 0.00 |
| 2 | 0.2 | 5 | 0.610 | 94.65[3] | 341 | 5 | 5 mL DDI | 0.431[3] | 83.43[3] | 1.48[3] | 3.94[3] |
| 3 | 0.2 | 5 | 0.610 | 94.17[3] | 342 | 5 | 5 mL DDI | 0.295[3] | 45.75[3] | 3.25[3] | 2.83[3] |
| 4 | 0.2 | 5 | 0.610 | 93.65[3] | 343 | 5 | 5 mL DDI | 0.415[3] | 52.97[3] | 2.16[3] | 3.74[3] |
| 5 | 0.2 | 5 | 0.610 | 93.04[3] | 344 | 5 | 5 mL DDI | 0.412[3] | 55.74[3] | 1.74[3] | 2.72[3] |
| 6 | 0.2 | 5 | 0.610 | 92.18[3] | 345 | 5 | 5 mL DDI | 0.234[3] | 90.45[3] | 1.68[3] | 26.14[3] |
| 7 | 0.2 | 5 | 0.590 | 74.86[1] | 346 | 2 | 5 mL MP | 0.399[1] | 73.91[1] | 22.32[1] | 2.69[1] |
| 8 | 0.2 | 5 | 0.590 | 71.17[1] | 347 | 2 | 5 mL MP | ND | 52.58[1] | 10.43[1] | ND |
| 9 | 0.2 | 5 | 0.590 | 67.57[1] | 348 | 2 | 5 mL MP | ND | 61.33[1] | 16.01[1] | ND |
| 10 | 0.2 | 5 | 0.595 | 72.29[1] | 349 | 2 | 5 mL MP | ND | 100.09[1] | 12.12[1] | ND |

TABLE 5-continued

Particle size determinations

| Run Number | Formulation (BUP) % | Flow Rate (mg/sec) | Target Resistance (ohms) | Energy (J) | MOUDI Number | Number of Actuations | Solvent and Volume | MMAD (microns) | Material Balance (%) | Throat Deposition (%) | Wall Losses (%) |
|---|---|---|---|---|---|---|---|---|---|---|---|
| 11 | 0.2 | 5 | 0.600 | 77.21[1] | 350 | 2 | 5 mL MP | ND | 79.28[1] | 3.08[1] | ND |
| 12 | 0.2 | 5 | 0.595 | 77.24[2] | 351 | 4 | 10 mL DDI | 0.464[2] | 81.82[2] | 2.94[2] | 5.76[2] |
| 13 | 0.2 | 5 | 0.595 | 71.95[2] | 352 | 4 | 10 mL DDI | 0.456[2] | 143.93[2] | 2.47[2] | 7.16[2] |
| 14 | 0.2 | 5 | 0.595 | 71.70[2] | 353 | 4 | 10 mL DDI | 0.417[2] | 133.08[2] | 0.00[2] | 0.00[2] |
| 15 | 0.2 | 5 | 0.595 | 71.17[2] | 354 | 4 | 10 mL MP | 0.416[2] | 90.90[2] | 4.55[2] | 17.45[2] |
| 16 | 0.2 | 5 | 0.595 | 71.32[2] | 355 | 4 | 10 mL DDI | 0.392[2] | 80.14[2] | 2.10[2] | 12.31[2] |
| 17 | 0.2 | 5 | 0.595 | 71.68[2] | 356 | 4 | 10 mL DDI | 0.451[2] | 71.86[2] | 0.00[2] | 27.18[2] |
| 18 | 0.2 | 5 | 0.595 | 71.32[1] | 357 | 2 | 5 mL MP | 0.424[1] | 94.10[1] | 2.33[1] | 3.61[1] |
| 19 | 0.2 | 5 | 0.595 | 71.37[1] | 358 | 2 | 5 mL MP | 0.450[1] | 89.79[1] | 1.98[1] | 3.48[1] |
| 20 | 0.2 | 5 | 0.595 | 71.22[1] | 359 | 2 | 5 mL MP | 0.446[1] | 82.30[1] | 3.01[1] | 2.64[1] |

[1] Mean of 2 actuations
[2] Mean of 4 actuations
[3] Mean of 5 actuations
ND—not determined

Example 3

Triazolam Aerosol

A suitable aerosol was generated using triazolam (8-chloro-6-(2-chlorophenyl)-1-methyl-4H-[1,2,4]triazolo[4,3-a][1,4]benzodiazepine) dissolved in propylene glycol (PG). Experiments were performed to determine if a chemically stable 0.5 μm triazolam aerosol could be generated using a 28 gauge, 44 mm long steel capillary using a flow rate of 5 mg/sec. The aerosol particle size was determined and the chemical stability of triazolam in the generated aerosol was evaluated. Triazolam was purchased from Sigma Aldrich Chemical Co. Propylene glycol was purchased from Dow Chemical Co.

Forced Degradation Studies

Triazolam was dissolved in acidic and basic solutions and heated to 50 degrees Celsius for 1 hour to promote acid and base catalyzed hydrolysis. Triazolam was also subjected to peroxide with heating to 50 degrees Celsius for 1 hour to promote oxidation. As a final stability check, solid triazolam was subjected to heating with a differential scanning calorimeter. Conditions were optimized to produce thermal degradation products by heating to 350 degrees Celsius.

Sham Determinations

Sham determinations were performed for each set of experiments to determine an "expected" amount of active per CAG activation. This was performed by running the equipment at a target resistance of 0.2 ohms, which pumped out the solution of triazolam in PG as a liquid instead of an aerosol. This was collected on a Kimwipe which was placed into sample solvent and sonicated. The process was performed in triplicate and was analyzed with other analytical samples. Triazolam was dissolved in PG at a concentration of approximately 0.1%.

Dose Capture and Degradation Determinations

Dose capture determinations were conducted (Table 6). For dose capture runs 1-3, the device was actuated once, the aerosol collected in 10 mL of sample solvent and analyzed using the "stability indicating" method. Runs 4-9 were performed as above except the device was actuated twice and collected in 10 mL of sample solvent. For runs 10-14, the device was actuated 3 times, the aerosol was collected in 5 mL of distilled deionized water, and analyzed for triazolam and degradation products using the "stability indicating" assay. Intact triazolam was calculated based upon prepared standards. The extent of degradation was evaluated by assuming that the degradation products had similar extinction coefficients as the parent at the wavelength of interest.

The investigations indicated that an energy of greater than about 80 J was required to aerosolize triazolam and minimize throat deposition. This was further refined to a target resistance of 0.605 ohms to provide an energy input of about 90 J. Using these parameters, 90% of the triazolam (Table 6, runs 10-14), as compared to sham experiments, was aerosolized and collected.

Triazolam was thermally stressed with a DSC to produce a degradation profile more representative of triazolam degradation after aerosolization via the CAG. Thermal degradation products were produced under the conditions stated above. This provided an indication of retention times for potential degradation products of triazolam after aerosolization using the CAG. The samples collected at a target resistance of 0.605 ohms were evaluated for degradation. An analyte with a retention time longer than triazolam was observed in all samples (standards, shams, and dose capture experiments). This peak was 6-8% of the peak area of triazolam, which is characteristic of an impurity.

Particle Size Determinations

Aerosol particle size was determined using the 10-stage MOUDI operated at 30 L/min. For MOUDI runs 1-4, the sample foils were placed in beakers, 5 mL of sample solvent was added, and the beakers swirled thoroughly. For the USP throat, 5 mL of sample solvent was added and shaken thoroughly. Wall losses were assessed by washing the MOUDI walls with a Kimwipe dipped in sample solvent. The same 5 mL of sample solvent was used to wash the walls of all the stages. The collected samples were analyzed using the assay method. For MOUDI runs 5-9, the procedure was the same as above except distilled deionized water was used in place of the sample solvent. This was done to allow for simultaneous PG particle size analysis. Two actuations were used for all MOUDI runs with the exception of MOUDI runs 1 and 7.

Figure 3:
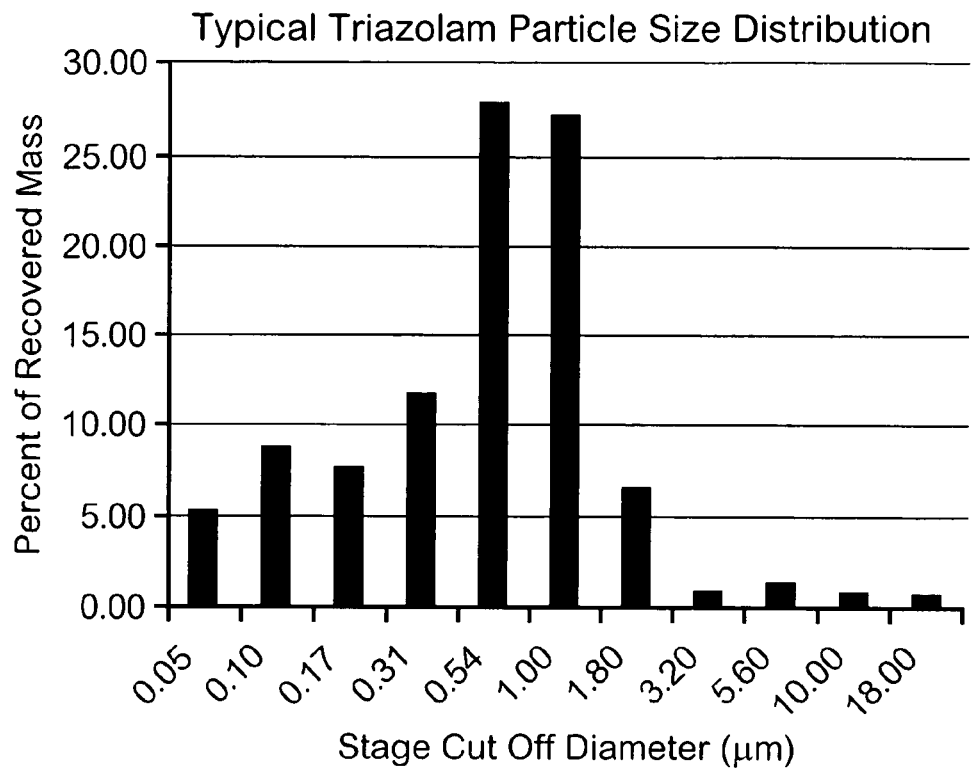
FIG. 3 shows a bar graph illustrating the typical triazolam particle size distribution.

Early dose capture experiments indicated that triazolam could be aerosolized and captured. Triazolam was stable upon heating and during aerosolization with the CAG. After determining energy requirements for aerosolizing triazolam, particle size determinations were performed (Table 7). At energies of approximately 70 J (runs 1 and 2), a large percentage, greater than 30%, of the recovered triazolam was found on the throat. At the refined target resistance of 0.605 ohms (runs 5-9), the energies were approximately 90 J. This produced aerosols (FIG. 3) having an average MMAD of approximately 0.46 microns. The average recovery for these experiments exceeded 99% and had throat depositions of less than 3%.

TABLE 6

Dose capture determinations

| Run Number | Formulation Triazolam % | Formulation Flow Rate (mg/sec) | Target Resistance (ohms) | Energy (J) | Air Flow Rate (L/min) | Dose Capture (%) |
|---|---|---|---|---|---|---|
| 1 | 0.1 | 5 | 0.590 | 74.20 | 0.5 | 99 |
| 2 | 0.1 | 5 | 0.600 | 85.58 | 0.5 | 109 |
| 3 | 0.1 | 5 | 0.610 | 93.77 | 0.5 | 86 |
| 4-6 | 0.1 | 5 | 0.590 | 74.62[1] | 0.5[1] | 90[1] |
| 7-9 | 0.1 | 5 | 0.600 | 85.07[1] | 0.5[1] | 95[1] |
| 10-14 | 0.1 | 5 | 0.605 | 90.59[2] | 0.5[2] | 90[2] |

[1]Mean of 6 determinations (3 dose captures of 2 actuations)
[2]Mean of 15 determinations (5 dose captures of 3 actuations)

TABLE 7

Particle size determinations

| Run Number | Formulation Triazolam % | Flow Rate (mg/sec) | Target Resistance (ohms) | Energy (J) | MOUDI Number | MMAD (microns) | Material Balance (%) | Throat Deposition (%) | Wall Losses (%) |
|---|---|---|---|---|---|---|---|---|---|
| 1 | 0.1 | 5 | 0.590 | 70.13 | 319 | 0.847 | 74.08 | 33.14 | ND |
| 2 | 0.1 | 5 | 0.590 | 70.55[3] | 320 | 0.642[3] | 108.22[3] | 39.28[3] | 15.51[3] |
| 3 | 0.1 | 5 | 0.600 | 83.54[3] | 321 | 0.378[3] | 104.22[3] | 2.96[3] | 11.04[3] |
| 4 | 0.1 | 5 | 0.595 | 78.38[3] | 322 | 0.414[3] | 98.50[3] | 3.66[3] | 6.69[3] |
| 5 | 0.1 | 5 | 0.605 | 87.98[3] | 335 | 0.511[3] | 102.10[3] | 2.43[3] | 20.44[3] |
| 6 | 0.1 | 5 | 0.605 | 86.62[3] | 336 | 0.431[3] | 96.32[3] | 1.35[3] | 12.27[3] |
| 7 | 0.1 | 5 | 0.605 | 89.01 | 337 | 0.483 | 107.02 | 2.87 | 4.59 |
| 8 | 0.1 | 5 | 0.605 | 88.07[3] | 338 | 0.444[3] | 91.60[3] | 2.47[3] | 2.78[3] |
| 9 | 0.1 | 5 | 0.605 | 87.40[3] | 339 | 0.446[3] | 101.09[3] | 1.97[3] | 2.33[3] |

[3]Mean of 2 actuations
ND—not determined

Example 4

Cyclobenzaprine Aerosol

A suitable aerosol was generated using cyclobenzaprine (3-(5H-Dibenzo[a,d]cyclohepten-5-ylidene)-N,N-dimethyl-1-propanamine) dissolved in propylene glycol (PG). Experiments were performed to determine if a chemically stable 0.5 µm cyclobenzaprine aerosol could be generated using a 28 gauge, 44 mm long steel capillary using a flow rate of 5 mg/sec. The aerosol particle size was determined and chemical stability of cyclobenzaprine in the generated aerosol was evaluated. Cyclobenzaprine was purchased from Sigma Aldrich Chemical Co. Propylene glycol was purchased by Dow Chemical Co.

Forced Degradation Studies

Cyclobenzaprine was subjected to heating with a differential scanning calorimeter. Conditions were optimized to produce thermal degradation products by heating to 300 degrees Celsius.

Sham Determinations

Sham determinations were performed for each set of experiments to determine an "expected" amount of active per CAG activation. This was performed by running the equipment at a target resistance of 0.2 ohms, which pumped out the solution of cyclobenzaprine in PG as a liquid instead of an aerosol. This was collected on a Kimwipe which was placed into sample solvent and sonicated. This process was performed in triplicate and was analyzed with other analytical samples. Cyclobenzaprine was dissolved in PG at a concentration of approximately 2%.

Dose Capture and Degradation Determinations

Dose capture determinations were conducted. The exact details may be found in Table 8, which lists each experiment, the number of actuations, the solvent and volume used, and the results. Intact cyclobenzaprine was calculated. The extent of degradation was evaluated by assuming that the degradation products had similar extinction coefficients as the parent at the wavelength of interest.

The investigations indicated that an energy of greater than about 70 J was required to aerosolize cyclobenzaprine and minimize throat deposition. This was further refined to a target resistance of 0.595 ohms to provide an energy input of about 73 J. Using these parameters, >95% of the cyclobenzaprine (runs 13-17), as compared to sham experiments, was aerosolized and collected. Analysis of the samples from runs 13-17 indicated an average degradation of less than 0.3%. This was in the form of multiple proposed degradation products.

Based upon the reproducible effective aerosolization and suitable particle size, it was concluded that cyclobenzaprine was a compound suitable for aerosolization.

Particle Size Determinations

Aerosol particle size was determined using the 10-stage MOUDI operated at 30 L/min. See Table 9, which lists each experiment, the number of actuations, the solvent and volume used, and the results. For the USP throat, 10 mL of sample solvent was added and shaken thoroughly. Wall losses were assessed by washing the MOUDI walls with a Kimwipe dipped in sample solvent. The same sample solvent was used to wash the walls of all the stages. The collected samples were analyzed using the assay method.

Figure 4:
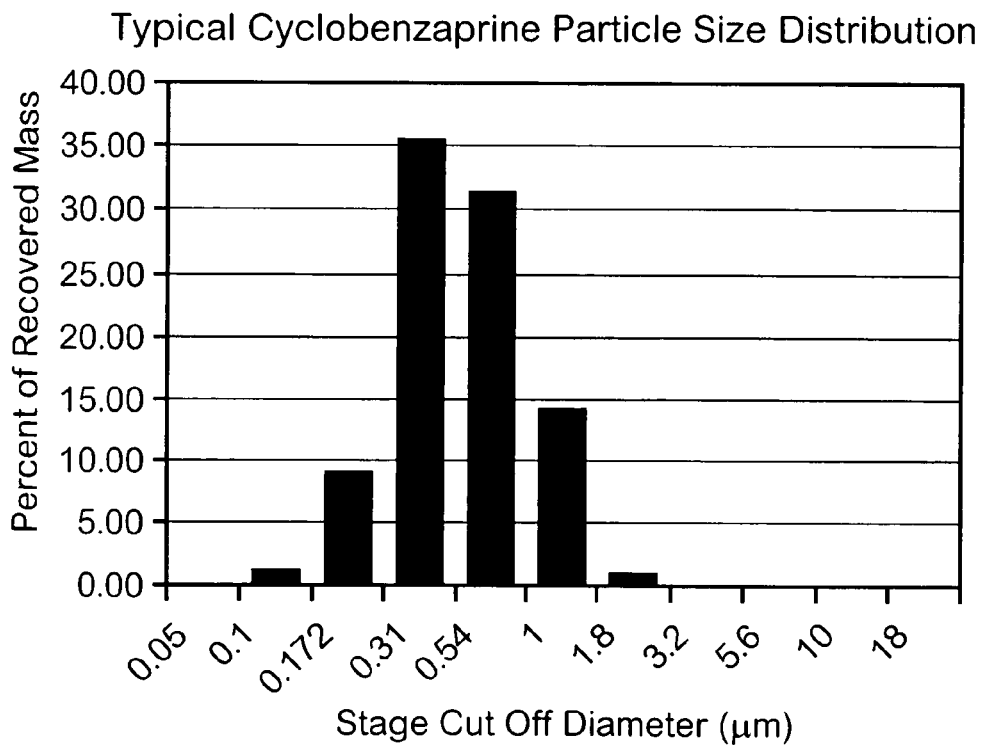
FIG. 4 shows a bar graph illustrating the typical cyclobenzaprine particle size distribution.

A stage was dropped for run 3 and the data from run 3 was not used in the final analysis. At the refined target resistance of 0.595 ohms (runs 1-6, excluding run 3), the energies were approximately 71 J. This produced aerosols (FIG. 4) having an average MMAD of approximately 0.33 microns. The average recovery for these experiments exceeded 93% and had throat depositions of less than 4%.

Example 5

Zolpidem Aerosol

A suitable aerosol was generated using zolpidem (N,N,6-Trimethyl-2-(4-methylphenyl)-imidazo[1,2-a]pyridine-3-acetamide) dissolved in propylene glycol (PG). Experiments were performed to determine if a chemically stable 0.5 μm zolpidem aerosol could be generated using a 28 gauge, 44 mm long steel capillary using a flow rate of 5 mg/sec. The aerosol particle size were determined and chemical stability of zolpidem in the generated aerosol was evaluated. Zolpidem was purchased from Sigma Aldrich Chemical Co. Propylene glycol was purchased from Dow Chemical Co.

Sham Determinations

Sham determinations were performed for each set of experiments to determine an "expected" amount of active per CAG activation. This was performed by running the equipment at a target resistance of 0.2 ohms. This essentially pumped out the solution of zolpidem in PG as a liquid instead of an aerosol. This was collected on a Kimwipe which was

TABLE 8

Dose capture and degradation determinations

| Run Number | Formulation Cyclobenzaprine % | Formulation Flow Rate (mg/sec) | Target Resistance (ohms) | Energy (J) | Air Flow Rate (L/min) | Number of Actuations | Solvent and Volume | Dose Capture (%) | Percent Degradation |
|---|---|---|---|---|---|---|---|---|---|
| 1 | 2.0% | 5 | 0.590 | 67.68 | 0.5 | 1 | 10 mL MP | 38.32 | ND |
| 2 | 2.0% | 5 | 0.600 | 78.64 | 0.5 | 1 | 10 mL MP | 202.88* | ND |
| 3 | 2.0% | 5 | 0.610 | 87.45 | 0.5 | 1 | 10 mL MP | 109.93 | ND |
| 4 | 2.0% | 5 | 0.590 | 67.97 | 0.5 | 1 | 10 mL MP | 36.58 | ND |
| 5 | 2.0% | 5 | 0.590 | 68.30 | 0.5 | 1 | 10 mL MP | 44.81 | ND |
| 6 | 2.0% | 5 | 0.590 | 68.53 | 0.5 | 1 | 10 mL MP | 42.17 | ND |
| 7 | 2.0% | 5 | 0.595 | 73.38 | 0.5 | 1 | 10 mL MP | 98.10 | ND |
| 8 | 2.0% | 5 | 0.595 | 73.89 | 0.5 | 1 | 10 mL MP | 90.47 | ND |
| 9 | 2.0% | 5 | 0.595 | 73.69 | 0.5 | 1 | 10 mL MP | 90.75 | ND |
| 10 | 2.0% | 5 | 0.600 | 78.28 | 0.5 | 1 | 10 mL MP | 101.97 | ND |
| 11 | 2.0% | 5 | 0.600 | 78.45 | 0.5 | 1 | 10 mL MP | 98.83 | ND |
| 12 | 2.0% | 5 | 0.600 | 78.58 | 0.5 | 1 | 10 mL MP | 97.73 | ND |
| 13 | 2.0% | 5 | 0.595 | 72.71 | 0.5 | 1 | 10 mL MP | 96.73 | 0.31 |
| 14 | 2.0% | 5 | 0.595 | 73.94 | 0.5 | 1 | 10 mL MP | 96.03 | 0.25 |
| 15 | 2.0% | 5 | 0.595 | 73.55 | 0.5 | 1 | 10 mL MP | 96.34 | 0.04 |
| 16 | 2.0% | 5 | 0.595 | 73.71 | 0.5 | 1 | 10 mL MP | 95.42 | 0.23 |
| 17 | 2.0% | 5 | 0.595 | 73.34 | 0.5 | 1 | 10 mL MP | 96.53 | 0.37 |
| 18 | 2.0% | 5 | 0.600 | 77.25 | 0.5 | 1 | 10 mL MP | 95.42 | 0.36 |

MP—mobile phase
ND—not determined
*aValue believed to be elevated due to carry-over in capillary

TABLE 9

Particle size determination

| Run Number | Formulation Cyclobenzaprine % | Flow Rate (mg/sec) | Target Resistance (ohms) | Energy (J) | MOUDI Number | Number of Actuations | Solvent and Volume | MMAD (microns) | Material Balance (%) | Throat Depositions (%) | Wall Losses (%) |
|---|---|---|---|---|---|---|---|---|---|---|---|
| 1 | 2.0 | 5 | 0.595 | 70.19 | 368 | 1 | 10 mL MP | 0.333 | 99.10 | 2.59 | 1.98 |
| 2 | 2.0 | 5 | 0.595 | 70.19 | 369 | 1 | 10 mL MP | 0.336 | 93.99 | 3.09 | 2.26 |
| 3 | 2.0 | 5 | 0.595 | 70.94 | 370 | 1 | 10 mL MP | $0.256^2$ | $61.98^2$ | $4.89^2$ | $1.99^2$ |
| 4 | 2.0 | 5 | 0.595 | 71.52 | 371 | 1 | 10 mL MP | 0.330 | 92.04 | 3.45 | 0.81 |
| 5 | 2.0 | 5 | 0.595 | 72.02 | 372 | 1 | 10 mL MP | 0.329 | 91.03 | 3.39 | 1.12 |
| 6 | 2.0 | 5 | 0.595 | 70.82 | 373 | 1 | 10 mL MP | 0.343 | 93.48 | 5.55 | 2.33 |

MP—mobile phase
[2]Stage seven dropped placed into sample solvent and sonicated. This process was performed in triplicate and was analyzed with other analytical samples. Zolpidem was dissolved in PG at a concentration of approximately 0.2%.

Dose Capture and Degradation Determinations

Dose capture determinations were conducted. See Table 10, which lists each experiment, the number of actuations, the solvent and volume used, and the results. Intact zolpidem was calculated. The extent of degradation was evaluated by assuming that the degradation products had similar extinction coefficients as the parent at the wavelength of interest.

The experiments indicated that an energy of greater than about 75 J was required to aerosolize zolpidem and minimize throat deposition. This was further refined to a target resistance of 0.600 ohms to provide an energy input of approximately 78 J. Using these parameters, >94% of the zolpidem expected (runs 5-9), as compared to sham experiments, was aerosolized and collected. Analysis of the samples from runs 5-9 indicated an average degradation of less than 0.1%. This was in the form of three proposed degradation products. The proposed degradation products were also observed in the sham.

Particle Size Determinations

Aerosol particle size was determined using the 10-stage MOUDI operated at 30 L/min. See Table 11, which lists each experiment, the number of actuations, the solvent and volume used, and the results. For the USP throat, 5 mL of sample solvent was added and shaken thoroughly. Wall losses were assessed by washing the MOUDI walls with a Kimwipe dipped in sample solvent. The same sample solvent was used to wash the walls of all the stages. The collected samples were analyzed using the assay method.

Figure 5:
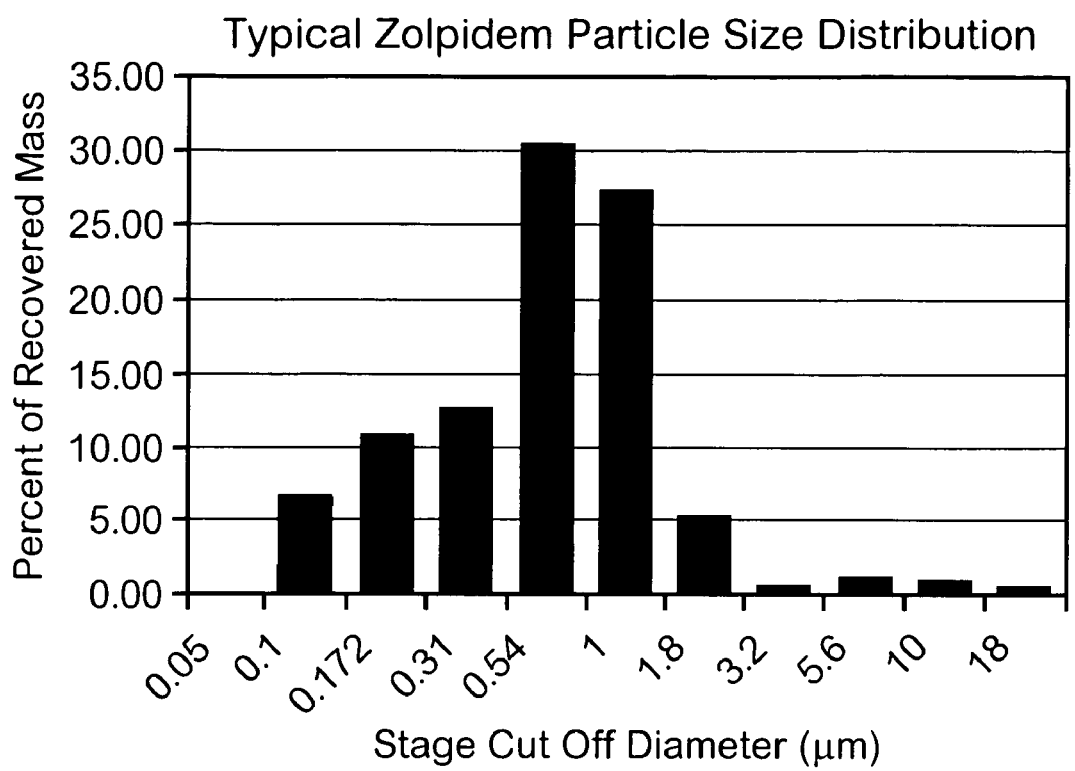
FIG. 5 shows a bar graph illustrating the typical zolpidem particle size distribution.

Early dose capture experiments indicated that zolpidem could be aerosolized and captured. After determining energy requirements for aerosolizing zolpidem, particle size determinations were performed (Table 11). At energies of approximately 75 J (runs 5-8), a small percentage of the recovered zolpidem was found on the throat. At the refined target resistance of 0.600 ohms (runs 5-8), the energies were approximately 75 J. This produced aerosols (FIG. 5) had an average MMAD of approximately 0.45 microns. The average recovery for these experiments exceeded 90% and had throat depositions of less than 4%.

Based upon the reproducible effective aerosolization and suitable particle size, it was concluded that zolpidem was a compound suitable for aerosolization.

TABLE 10

Dose capture and degradation determinations

| Run Number | Formulation Zolpidem % | Formulation Flow Rate (mg/sec) | Target Resistance (ohms) | Energy (J) | Air Flow Rate (L/min) | Number of Actuations | Solvent and Volume | Dose Capture (%) | Percent Degradation |
|---|---|---|---|---|---|---|---|---|---|
| 1 | 0.2 | 5 | 0.590 | 69.46 | 0.5 | 1 | 10 mL MP | 40.80 | ND |
| 2 | 0.2 | 5 | 0.600 | 78.08 | 0.5 | 1 | 10 mL MP | 145.30[1] | ND |
| 3 | 0.2 | 5 | 0.610 | 87.86 | 0.5 | 1 | 10 mL MP | 100.14 | ND |
| 4 | 0.2 | 5 | 0.610 | 93.11 | 0.5 | 1 | 5 mL MP | 82.00 | ND |
| 5 | 0.2 | 5 | 0.600 | 78.61 | 0.5 | 1 | 10 mL MP | 97.31 | 0.26 |
| 6 | 0.2 | 5 | 0.600 | 77.56 | 0.5 | 1 | 10 mL MP | 100.64 | 0.02 |
| 7 | 0.2 | 5 | 0.600 | 73.38 | 0.5 | 1 | 10 mL MP | 94.35 | 0.00 |
| 8 | 0.2 | 5 | 0.600 | 77.71 | 0.5 | 1 | 10 mL MP | 107.09 | 0.03 |
| 9 | 0.2 | 5 | 0.600 | 77.93 | 0.5 | 1 | 10 mL MP | 97.43 | 0.16 |

MP—mobile phase
ND—not determined
[1]Value believed to be elevated due to carry-over in capillary

TABLE 11

Particle size determination

| Run Number | Formulation Zolpidem % | Flow Rate (mg/sec) | Target Resistance (ohms) | Energy (J) | MOUDI Number | Number of Actuations | Solvent and Volume | MMAD (microns) | Material Balance (%) | Throat Deposition (%) | Wall Losses (%) |
|---|---|---|---|---|---|---|---|---|---|---|---|
| 1 | 0.2 | 5 | 0.600 | 75.52 | 360 | 1 | 5 mL MP | 0.404 | 101.56 | 0.21 | 0.90 |
| 2 | 0.2 | 5 | 0.600 | 76.05 | 361 | 1 | 5 mL DDI | 0.431 | 93.04 | 1.95 | 1.35 |
| 3 | 0.2 | 5 | 0.590 | 66.10 | 362 | 1 | 5 mL DDI | ND | ND | ND | ND |
| 4 | 0.2 | 5 | 0.590 | 66.21 | 363 | 1 | 5 mL DDI | 0.464 | 64.51 | 5.36 | 1.68 |
| 5 | 0.2 | 5 | 0.600 | 76.00 | 364 | 1 | 5 mL MP | 0.481 | 100.06 | 3.97 | 6.18 |
| 6 | 0.2 | 5 | 0.600 | 75.57 | 365 | 1 | 5 mL MP | 0.459 | 90.77 | 0.12 | 2.67 |
| 7 | 0.2 | 5 | 0.600 | 74.97 | 366 | 1 | 5 mL MP | 0.420 | 97.74 | 0.62 | 3.55 |
| 8 | 0.2 | 5 | 0.600 | 74.96 | 367 | 1 | 5 mL MP | 0.421 | 95.83 | 1.27 | 3.85 |

DDI—deionized, distilled water
ND—not determined

Example 6

Preferred Emitted Doses and Fine Particle Fractions

In preferred embodiments, the emitted doses (i.e., the aerosolized dose) and the fine particle fractions of the emitted doses for buspirone, buprenorphine, triazolam, cyclobenzaprine and zolpidem are summarized in Table 12 as follows:

TABLE 12

Emitted Dose and Fine Particle Fraction

| Active | Formulation (% w/v) | Avg. Emitted Dose per Actuation (mcg) | Emitted Dose Std Dev | Avg. FPF (% of Emitted) | FPF Std Dev | Sample Size (n) | # Actuations |
| --- | --- | --- | --- | --- | --- | --- | --- |
| Buprenorphine | 0.2 | 89.23 | 3.90 | 94.02 | 0.75 | 3 | 2 |
| Buspirone | 2.0 | 1010.44 | 30.83 | 91.60 | 2.29 | 5 | 1 |
| Cyclobenzaprine | 2.0 | 836.16 | 35.00 | 94.35 | 1.39 | 5 | 1 |
| Triazolam | 0.1 | 46.46 | 3.03 | 86.16 | 8.58 | 4 | 2 |
| Zolpidem | 0.2 | 92.55 | 4.01 | 93.25 | 3.73 | 4 | 1 |

Sample size equals the number of runs used to determine the average data.
actuations equals the number of 10 second actuations of the device used in each run.
FPF—fine particle fraction, the percent of total dose collected less than 5.6 microns.

The above-described exemplary modes of carrying out the invention are not intended to be limiting. It will be apparent to those of ordinary skill in the art that modifications thereto can be made without departure from the spirit and scope of the invention as set forth in the accompanying claims.

For instance, while a heated capillary tube has been described as the preferred construction of the capillary passage, the capillary passage can comprise one or more channels in a laminate having a heater arranged along the channel(s), multiple capillary tube arrangements, a passage having a heater located inside the passage, coaxial arrangements including an annular channel for fluid flow, or the like.

What is claimed is:

1. A method of generating an aerosol comprising:
   supplying a liquid aerosol formulation to a capillary-sized flow passage,
   heating the liquid aerosol formulation in the capillary-sized flow passage so as to volatilize a liquid component thereof and form a vapor which exits from an outlet of the capillary-sized flow passage, and
   contacting the vapor with a gaseous medium so as to form an aerosol,
   wherein the liquid aerosol formulation includes at least one thermally stable active ingredient selected from the group consisting of buprenorphine, pharmaceutically acceptable salts and esters thereof.

2. The method of claim 1, wherein the gaseous medium comprises air, and the aerosol comprises propylene glycol-containing particles having an MMAD of less than 3 μm.

3. The method of claim 1, wherein the aerosol comprises buprenorphine particles having an MMAD of less than 3 μm.

4. The method of claim 1, wherein the aerosol is formed in a mouthpiece of a handheld inhaler.

5. The method of claim 1, wherein the aerosol includes particles of the thermally stable active ingredient having an MMAD of 0.1 to 2.5 μm.

6. The method of claim 1, wherein the capillary-sized flow passage is heated by a resistance heater located in a handheld inhaler, the hand-held inhaler including a power supply and control electronics which controls supply of electrical power to the resistance heater as a function of a resistance target in a range of 0.5 to 1 ohm.

7. An aerosol generator comprising:
   a liquid supply providing a liquid aerosol formulation comprising at least one thermally stable active ingredient selected from the group consisting of buprenorphine, pharmaceutically acceptable salts and esters thereof;
   a capillary-sized flow passage in fluid communication with the liquid aerosol formulation from the liquid supply; and
   a heater operable to heat the liquid aerosol formulation in at least a portion of the capillary-sized flow passage sufficiently to vaporize the liquid aerosol formulation and generate an aerosol containing the active ingredient.

8. The aerosol generator of claim 7, wherein the aerosol generator is a hand-held inhaler having a mouthpiece, wherein the capillary-sized flow passage has an outlet in fluid communication with an interior of the mouthpiece.

9. The aerosol generator of claim 7, wherein the heater is a resistance heater comprising a section of a metal capillary tube, and the capillary-sized flow passage comprises the interior of the metal capillary tube.

10. The aerosol generator of claim 7, wherein the aerosol generator is a hand-held inhaler having a power supply and control electronics which controls supply of electrical power to the heater as a function of a control parameter selected to achieve boiling of the liquid aerosol formulation in the capillary-sized flow passage.

11. The aerosol generator of claim 7, wherein the liquid supply comprises a reservoir containing the liquid aerosol formulation under a pressure of no greater than about atmospheric pressure.

* * * * *